United States Patent [19]

Volkmann

[11] Patent Number: 4,864,046
[45] Date of Patent: Sep. 5, 1989

[54] PROCESS FOR OPTICALLY ACTIVE 3-THIOLANYL SULFONATE ESTERS

[75] Inventor: Robert A. Volkmann, Mystic, Conn.

[73] Assignee: Pfizer Inc., New York, N.Y.

[21] Appl. No.: 308,868

[22] Filed: Feb. 9, 1989

[51] Int. Cl.[4] .......................................... C07C 141/02
[52] U.S. Cl. ........................................ 558/46; 549/66
[58] Field of Search ......................................... 558/46

[56] References Cited

U.S. PATENT DOCUMENTS

| | | | |
|---|---|---|---|
| 2,581,443 | 1/1952 | Reynolds | 558/46 |
| 2,726,162 | 12/1955 | Allen | 558/46 |
| 3,041,241 | 6/1962 | Timmis | 558/46 |

Primary Examiner—Alan Siegel
Attorney, Agent, or Firm—Peter C. Richardson; J. Trevor Lumb; Robert K. Blackwood

[57] ABSTRACT

Intermediates and a stepwise process for the conversion of ethyl 4-chloro-3R-hydroxybutyrate to optically active compounds of the formula

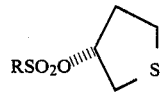

wherein R is $(C_1-C_3)$alkyl, phenyl or tolyl. The later compounds are in turn useful as an intermediate in the preparation of penem antibiotic 5R,6S-6-(1R-hydroxyethyl)-2-(1R-oxo-3S-thiolanylthio)-2-penem-3-carboxylic acic and corresponding pharmaceutically acceptable salts and esters.

3 Claims, No Drawings

PROCESS FOR OPTICALLY ACTIVE 3-THIOLANYL SULFONATE ESTERS

BACKGROUND OF THE INVENTION

The present invention is directed to intermediates and a stepwise process for the conversion of ethyl 4-chloro-3R-hydroxybutyrate, of the formula (II) below, to optically active 3-thiolanyl sulfonate esters of the formula

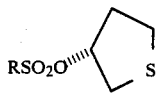
(I)

wherein R is $(C_1-C_3)$alkyl, phenyl or tolyl.

The compounds of formula (I) are particularly valuable intermediates in the preparation of certain penem antibiotics. Thus, antibacterial 5R,6S-6-(1R-hydroxyethyl)2-(cis-1-oxo-3-thiolanylthio)-2-penem-3-carboxylic acid, which is a diastereomeric mixture of two compounds, was earlier disclosed as a valuable antibacterial substance by Hamanaka, U.S. Pat. No. 4,619,924; while Volkmann et al., in U.S. Pat. No. 4,739,047, have disclosed an alternative synthesis for that substance. More recently, the preferred diastereoisomer [5R,6S-6-(1R-hydroxyethyl)-2-(1R-oxo3S-thiolanylthio)-2-penem-3-carboxylic acid]and a process therefor, have been identified and disclosed in my International Application No. PCT/US87/01114, designating inter alia the United States of America, published on Nov. 17, 1988 as WO-88/08845. Key to synthesis of this diastereoisomer is the optically active intermediate of the formula (I), earliest prepared by the following sequence:

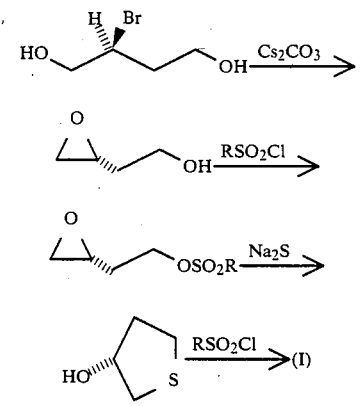

More recently, in commonly assigned, copending U.S. patent application, Ser. No. 07/183,102, filed Apr. 19, 1988, Urban describes a multistep synthesis of the compound of the formula (I) from D-methionine, as follows:

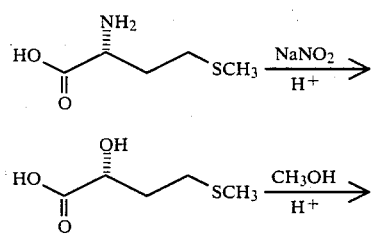

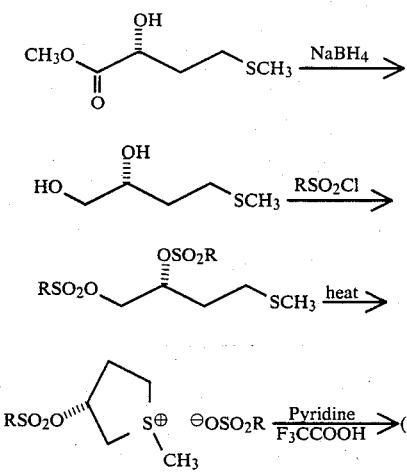

We have now discovered that the optically active compounds of the formula (I) are most conveniently and readily prepared by a three step process from ethyl 4-chloro-3R-hydroxybutyrate, an optically active compound now easily available in 97% yield by hydrogenation of ethyl 4-chloroacetoacetate over an optically active ruthenium catalyst according to the method of Kitamura, et al., Tetrahedron Letters, vol. 29, pp. 1555–1556, 1988.

The presently prepared thiolanyl sulfonate esters of the formula (I) are used in the synthesis of the above identified diastereomeric penem antibiotic according to methods which are available to the public in my published International patent application WO-88/08845, cited above, which also teaches the advantageous utility of this penem antibiotic.

SUMMARY OF THE INVENTION

The present invention is directed to a process for the preparation of an optically active compound of the formula

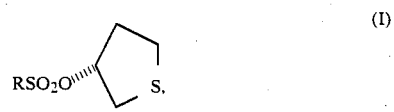
(I)

wherein R is $(C_1-C_3)$alkyl, phenyl or tolyl, which comprises the steps of:

(a) hydride reduction of an optically active ester of the formula

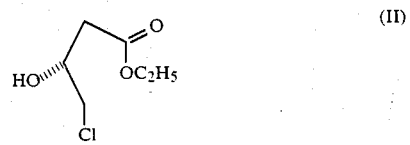
(II)

with an amount of a hydride reducing agent capable of reducing an ester to an alcohol in a reaction-inert solvent to form an optically active diol of the formula

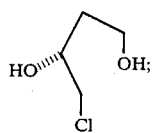

(III)

(b) reacting said diol in the same or another reaction-inert solvent with at least 2 molar equivalents of an activated form of a sulfonic acid of the formula RSO₂OH in the presence of at least 2 equivalents of a tertiary amine to form an optically active disulfonate of the formula

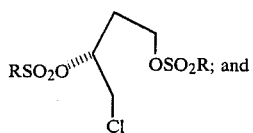

(IV)

(c) reacting said disulfonate with a sulfide salt in the same or another reaction-inert solvent to form the compound of the formula (I).

While conventional activation as a mixed anhydride, or with such reagents as dicyclohexylcarbodiimide or 1,1'-carbonyldiimidazole is generally satisfactory, the preferred activated form of the sulfonic acid in step (b) is the sulfonyl chloride, RSO₂Cl. The preferred values of R are methyl and p-tolyl. Alkali metal sulfides, particularly Na₂S, are the preferred sulfide salts in step (c). It is further preferred to use an iodide salt to catalyze the reaction of step (c). Most preferred for this purpose is tetrabutylammonium iodide. A variety of hydride reducing agents are generally useful in step (a). However, milder agents such as LiBH₄ are preferred, using amounts and solvents as defined below.

The present invention is also directed to the above compounds of the formula (III) and (IV), written in combined form as

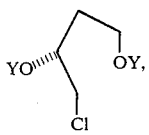

(III)

wherein Y is hydrogen or RSO₂— and R is (C₁₋C₃)alkyl, phenyl or tolyl. When Y is RSO₂—, the preferred values of R are methyl and p-tolyl.

As employed above and elsewhere herein, the expression "reaction-inert solvent" refers to a solvent which does not interact with starting materials, reagents, intermediates or products in a manner which adversely affects the yield of the desired product.

DETAILED DESCRIPTION OF THE INVENTION

The present preparation of optically active thiolanyl sulfonate esters of the formula (I) from ethyl (R)-4-chloro-3-hydroxybutyrate (II) is readily carried out via the intermediates (R)-4-chlorobutane-1,3-diol (III) and disulfonate ester (IV), using the sequential steps of (a) hydride reduction, (b) bis-sulfonylation and (c) sulfide displacement/cyclization.

The hydride reduction step is carried out generally using at least two chemical equivalents of a conventional hydride reducing agent. For a review of such agents, see House, Modern Synthetic Reactions, 2nd ed., W. A. Benjamin Inc., Menlo Park, CA, pp. 45–105. The preferred agent in the present case is LiBH₄, in a reaction-inert solvent which will generally be aprotic (preferably a relatively polar ether such as tetrahydrofuran, dioxan or 1,2-dimethoxyethane). At least 2 chemical equivalents of LiBH₄ are used (i.e., 0.5 mol of LiBH₄/mol of ester substrate). Temperature is not particularly critical, but temperatures in the range of about 0°–30° C. are preferred.

The conversion of the diol to bis-sulfonate ester is also carried out in a conventional manner, preferably by combining the diol (II) with substantially 2 molar equivalents of a sulfonyl chloride of the formula RSO₂Cl (where R is as defined above) in a reaction-inert solvent (such as CH₂Cl₂ or tetrahydrofuran) in the presence of at least two molar equivalents of a tertiary amine such as triethylamine. For this generally exothermic reaction, temperatures below ambient (e.g., 10° to −30° C.) are preferred. The exotherm and temperature can be controlled in part by the rate of addition of the acid chloride. In a variation of this process, an excess of pyridine is used as both tertiary amine and solvent.

The sulfide displacement/cyclization step in which sulfide reacts to form the thiolane ring (by displacement of the 1-sulfonate ester group and the 4-chloro group) is carried out under conditions characteristic of nucleophilic displacement reactions in general, particularly with respect to the initial biomolecular displacement of either 4-chloro or the 1-sulfonate group, where the rate is favored by higher concentrations of the reactants and completeness of reaction is favored by use of an excess of one of the reagents (in this case usually the sulfide). However, the second stage cyclization is a zero order, intramolecular displacement, where the rate will be substantially independent of concentration, but where increasingly high concentrations will favor formation of undesired dimer, or even polymer. Either stage of this reaction is favored by the use of iodide as catalyst. When a preferred alkali metal sulfide (e.g., Na₂S) is used as reagent, the preferred iodide salt is tetrabutylammonium iodide. Solvent is not critical in this reaction, although acidic solvents are generally to be avoided so as to maintain the sulfide and intermediate mercaptide in more reactive anionic form. Temperature is not critical; it should be high enough that the reaction proceeds to completion within a reasonable period of time, but not so high as to lead to undue decomposition. Temperatures in range of about 40°–100° C. are particularly well suited in the present case.

The following examples are given by way of illustration and are not to be construed as limitations of this invention, many variations of which are possible within the scope and spirit thereof.

EXAMPLE 1

(R)-4-Chlorobutane-1,3-diol

In a 500 ml 3-neck flask under nitrogen, ethyl (R)-4-chloro-3-hydroxybutyrate (17.33, 0.104 mol) is dissolved in 100 ml of tetrahydrofuran. The solution is cooled to 0° C. and a tetrahydrofuran solution containing lithium borohydride (2.0 M) (65 ml, 0.130 mol) is added dropwise over a 60 minute period. The ice bath is removed and the solution is stirred at 23° C. for 24 hours. The reaction is cooled to 0° C. and methanol added. Methanolic HCl is added and the crude reaction is concentrated in vacuo. To the crude product is added methanol and the reaction azeotroped (3×500 ml) to remove methyl borate. The crude white solid is partitioned between ethyl acetate (400 ml) and water (100 ml). The aqueous layer is saturated with NaCl and extracted with ethyl acetate (400 ml). The combined organic layers are dried over MgSO4 and stripped in vacuo to yield title product.

EXAMPLE 2

(R)-4-Chloro-3-(methanesulfonyloxy)butyl Methanesulfonate

In a 500 ml 3-neck flask under nitrogen, title product of preceding Example (10.7 g, 0.086 mol) is dissolved in 175 ml of CH2Cl2) The solution is cooled to −30° C. Triethylamine (17.4 g, 24 mls, 0.172 mole) is added followed by mesyl chloride (19.7 g, 13.3 ml, 0.172 mole). The solution is stirred at −20° to −15° C. for one hour and then poured over 600 ml of crushed ice and stirred for ten minutes. The separated aqueous layer is extracted with methylene chloride (1×200 ml). The combined organic layers are washed with 1N HCl (1×200 ml), saturated NaHCO3 (2×200 mls) and brine (1×200 ml), dried over MgSO4, and stripped in vacuo to afforded present title product.

To prepare (R)-4-chloro-3-(p-toluenesulfonyloxy)butyl p-toluenesulfonate, a molar equivalent of p-tolyl chloride is substituted for the mesyl chloride.

EXAMPLE 3

(R)-3-Thiolanyl Methanesulfonate

Title product of the preceding Example (2.5 g, 0.0089 mol) is dissolved in 25 ml of tetrahydrofuran under N2. Sodium sulfide nonahydrate (2.35 g, 0.0098 mol) and then tetrabutylammonium iodide (0.100 g, 0.0003 mol) are added. After heating at 50° C. for 76 hours, the reaction mixture was cooled, stripped in vacuo, diluted with 200 ml CHCl3, washed with H2O(2×100 ml) and then brine (1×100 ml), dried over MgSO4, and stripped in vacuo to yield present title product. If desired, this product is purified by chromatography on silica gel using CHCl3 as eluant.

By the same method the bis-p-tolyl ester of the preceding Example is converted to (R)-3-thiolanyl p-toluenesulfonate.

I claim:

1. An optically active compound of the formula

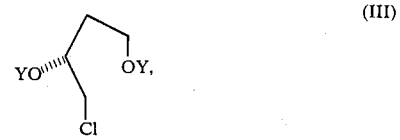

(III)

wherein Y is RSO2— and R is (C1-C3) alkyl, phenyl or tolyl.

2. The compound of claim 1 wherein R is methyl.

3. The compound of claim 1 wherein R is p-tolyl.

* * * * *